United States Patent [19]

Bisping

[11] Patent Number: 4,799,499

[45] Date of Patent: Jan. 24, 1989

[54] IMPLANTABLE ELECTRODE WITH ACTIVE FIXATION MEANS

[76] Inventor: Hans-Jürgen Bisping, Tittardshang 12, 5100 Aachen, Fed. Rep. of Germany

[21] Appl. No.: 894,877

[22] Filed: Aug. 8, 1986

[30] Foreign Application Priority Data

Aug. 17, 1985 [DE] Fed. Rep. of Germany ....... 3529578

[51] Int. Cl.⁴ ................... A61N 1/00; H05G 00/00
[52] U.S. Cl. ..................... 128/785; 128/419 P
[58] Field of Search ............... 128/642, 644, 419 C, 128/784, 785, 786, 791, 419 P

[56] References Cited

U.S. PATENT DOCUMENTS 3,835,864 9/1974 Rasor et al. .............. 128/419 P
4,233,992 11/1980 Bisping ..................... 128/786

FOREIGN PATENT DOCUMENTS 2732547 2/1979 Fed. Rep. of Germany ...... 128/785

Primary Examiner—Francis J. Jaworski
Assistant Examiner—George Manuel
Attorney, Agent, or Firm—Leitner, Greene & Christensen

[57] ABSTRACT

An implantable lead assembly to electrically stimulate the heart from a stimulus generator has an electrode head with a surface portion conducive to electrical stimulation, the head having a contour concentric with the axis except along a portion indented toward the axis to form a recess in the head. A conductive lead fastened to the head electrically connects the stimulation-conducive surface portion to the stimulus generator. A rigid hook is secured in fixed relation to the head with the curved portion of the hook lying at all times substantially within the recess and the tip of the hook normally unrestrained to project at all times at least slightly from the recess to engage heart tissue when the head is rotated about the axis by twisting the lead in the direction in which the tip is pointed.

17 Claims, 2 Drawing Sheets

IMPLANTABLE ELECTRODE WITH ACTIVE FIXATION MEANS

BACKGROUND OF THE INVENTION

1. Field of the Invention

The present invention relates generally to cardiac stimulation, and more particularly to an implantable electrode for stimulating and/or sensing electrical activity of the heart and employing an active fixation mechanism to secure the electrode in position relative to the cardiac tissue with which the electrode is intended to interact.

2. Prior Art

Patent publication DE No. 27 32 547 A1 of the Federal Republic of Germany illustrates the current state of the technology pertaining to active fixation of electrodes designed for implantation in a chamber of the heart for stimulating the cardiac muscle. According to the invention described in that publication, a fixing hook is associated with the electrode head of a catheter led and is arranged to be movable relative to the head. During the insertion phase the fixing hook, which possesses an intrinsic spring action, is restrained in a retracted position within the outer contour of the electrode head such that the overall lead assembly is readily advanced through the vein. The fixing hook may be held under this restraint by various means, for example by means of a blocking wire, and upon release, the tip of the hook is thrust to a position outside the contour of the electrode head. If necessary, the thrusting of the fixing hook tip into this position may be accomplished with the aid of further triggering means. In any event, the fixing hook is released by the implanting physician when the electrode is determined to be properly positioned within the selected chamber of the heart. In the released state, the fixing hook may be engaged in the cardiac tissue by twisting the electrode lead.

The practical implementation of such a lead with endocardial electrode and associated fixing hook is not achieved without difficulty, owing to the necessarily small dimensions of the electrode head and the lead. Considerable care is required in the manufacturing process to provide an active fixation mechanism in which the fixing hook is held within the outer contour of the electrode head for subsequent precise release.

It is a principal object of the present invention to provide an active fixation mechanism for an implantable electrode which avoids such disadvantages.

A more specific object of the present invention is to provide an active fixation electrode which can be readily manufactured in a simple manner, while retaining the desirable aspects of ease of insertion and engagement with cardiac tissue so as to be secure against dislodgement and to ensure good electrical stimulation.

SUMMARY OF THE INVENTION

The above and other objects of the invention are achieved by providing at least one fixing hook which is arranged to be stationary relative to the electrode head and which, through the selection of a suitable material and or design, is essentially rigid; with the tip or end of the hook conforming closely to the outer contour of the electrode head and lying within or adjacent to a recessed region of the electrode head and/or the lead. As will be understood from the present disclosure, several fixing hooks of such characterization may be distributed over the periphery of the electrode head.

Contrary to expectations, it has been found that an electrode employing such a firm, rigid fixing hook may nevertheless be introduced into a cardiac chamber without significant problems. Moreover, it is not necessary that the fixing hook lie entirely within the outer contour of the electrode head; indeed, it may protrude slightly. However, the protruding end should conform rather closely to the curvature of the outer contour of the electrode head. It is also important that a recess be provided in the region of the end of the fixing hook on the electrode head or, subject to the design, on the electrode lead. For fixing, the entire electrode is turned by twisting the lead after insertion, thereby allowing a sufficient quantity of tissue to be engaged by the fixing hook in conjunction with the recess, so that the electrode is securely retained in proper position by the engaged tissue.

According to an embodiment of the invention, the electrode head has a necked-down portion or bridge of reduced cross-section to provide the recess in the region of the fixing hook. This neck may be concentric with the axis of the electrode or the lead, but preferably is eccentric to that axis and directly adjoins the outer contour of the electrode head. Preferably also, the distance between confronting surfaces of the neck and the fixing hook tip is slightly greater than or equal to the difference between the radius of the electrode head and the diameter of the fixing-hook wire. The recess has an axial length in the region of the tip of the fixing hook equal to or greater than sixty-five percent of the diameter of the electrode head, and preferably eighty percent. These dimensions of the recess have been found to be particularly favorable and advantageous.

The recess should also extend circumferentially through an angle of about 270 degrees for cooperation with the fixing hook, and the tip of the fixing hook should be positioned at an angle less than or equal to 130 degrees relative to the beginning of the recess advancing in the direction of rotation. It is desirable that the surfaces of the neck be rounded in both the axial and circumferential directions, to provide smooth transitions as the head is rotated to engage tissue between the hook and the neck.

The fixing hook may be fastened to the electrode head in any desired manner, such as by insertion into a bore, groove or the like in the neck portion. Preferably, the open end of the bore or groove lies in the region of the recess, so that only a slight bending of the fixing hook is necessary The tip of the fixing hook may be rounded or pointed, with its furthermost point lying at the center or the outer or inner surface of the wire forming the hook. It is important to seek an optimum between secure engagement of the fixing hook with the cardiac tissue and ease of insertion of the lead through the vein into the selected chamber of the heart. A factor in that effort is the location of the hook, and more precisely the hook tip, relative to the outer contour of the electrode head, that is, whether the hook lies within the outer contour or protrudes beyond it.

According to a feature of the invention, the stimulation surface of the electrode may lie at the electrode tip and additionally or alternatively at the outer contour of the electrode within the band encompassing the tip of the fixing hook. Also, a portion of the surface of the neck confronting the inner surface of the hook wire may be a stimulation surface, to take advantage of its intimate contact with the tissue upon fixation of the electrode. Depending on design preferences, the fixing hook may be electrically insulated or conductive.

According to an alternative embodiment, the fixing hook has a spiral shape and is fastened between the electrode head and the lead. Here again, the electrode head may have a concentric or eccentric neck forming the recess in the region of the tip of the fixing hook. In this embodiment, the end of the fixing hook spiral to be fastened to the lead may have a smaller diameter than the end of the spiral constituting the tissue-engaging hook tip, and may be lodged between a portion of the lead and a portion of the electrode head.

As previously noted herein, further fixing hooks may be employed, similar to the fixing hooks thus far described but axially spaced therefrom, to accomplish further engagement of the cardiac tissue.

The distance between the tip of the electrode head and the tip of the nearest fixing hook has considerable influence on ease of insertion of the lead and secure engagement of the electrode.

BRIEF DESCRIPTION OF THE DRAWINGS

The above and still further objects, features and attendant advantages of the invention will become apparent to those of ordinary skill in the field to which the invention pertains by reference to the ensuing detailed description of preferred embodiments, in conjunction with the accompanying drawings in which.

DETAILED DESCRIPTION OF THE PREFERRED EMBODIMENTS

Figure 1:
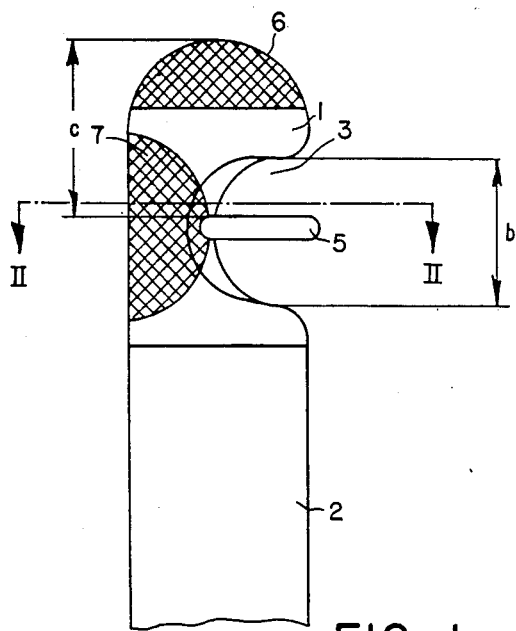
FIG. 1 is a side view of an electrode head and portion of the catheter lead of one embodiment of the invention.
Figures 2, 3:
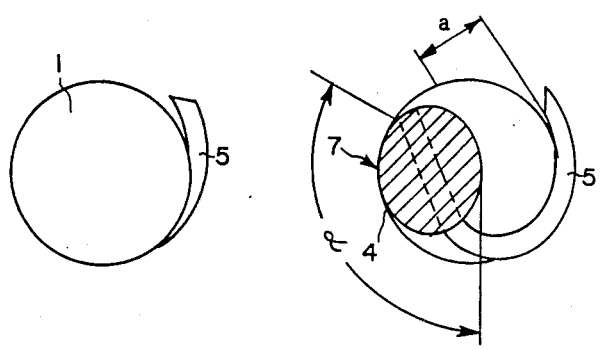
FIG. 2 is a sectional view of the electrode head taken through the plane II—II of FIG. 1.
FIG. 3 is a top view of the electrode head in the embodiment of FIG. 1.

Referring now to FIGS. 1, 2 and 3, the embodiment of the invention illustrated in those FIGS. comprises an electrode head 1 which is electrically and mechanically connected in a conventional manner to a catheter lead 2. The electrode head and the catheter lead are of a diameter suitable to allow insertion of the overall lead assembly through a vein (e.g., the superior vena cava) such that the electrode head may be positioned in the desired chamber of the patient's heart. The lead serves to couple the electrode head to a source of electrical stimulation, such as a pacemaker pulse generator, for delivery of electrical impulses to excitable cardiac tissue.

The electrode head has a recess 3 defined by a neck region 4 of reduced cross-section relative to that of the head, as most clearly seen in FIG. 2. The neck region 4, and thus the recess 3, extends a distance b along the axis of the electrode head equal to or greater than 65% of the diameter of the head at a region of full cross-section, and preferably 80% of that diameter.

It will be observed from FIGS. 1 and 2 that neck 4 is eccentric with respect to the axis of electrode head 1, and that a portion of its surface is coincident with the outer surface (and accordingly, the outer contour) of the head. While an eccentrically disposed neck portion is preferred, a neck portion concentric with the axis of the electrode head or having a somewhat lesser degree of eccentricity may alternatively be employed as will be noted presently in the description of the embodiments of FIGS. 4 and 5. The surface of the neck portion is finished to avoid any sharp edges or corners.

A fixing hook 5 is fastened to the electrode head 1 such that the hook tip is disposed in or in the vicinity of recess 3 for cooperation therewith when the electrode is to be affixed within the selected chamber of the heart. In this embodiment, the fixing hook 5 is fastened to the electrode head in the neck region 4 such that the hook lies entirely within a plane substantially bisecting the recess 3 axially, or at substantially the deepest point of the recess. The axial distance c between the tip of the electrode and the tip of the fixing hook is selected to optimize the ease of insertion of the lead and engagement of the hook with tissue, this distance preferably being greater than or equal to the diameter of the electrode head.

A simple bending of the wire (for example, rigid spring wire) of which the hook is composed suffices to form the desired curvature thereof. The amount of bending required may be reduced according to the orientation of the bore in which the hook wire is inserted, a preferred orientation being represented in FIG. 2. The fixing hook may be securely fastened to the head by welding, soldering, pressing, gluing or the like depending on the nature of the materials and whether the hook is electrically insulated.

The fixing hook is bent such that the curvature of the hook substantially conforms to the outer contour of the electrode head, although the tip of the hook may be allowed to extend slightly beyond that contour as illustrated in FIGS. 2 and 3. The distance a (FIG. 2) between the inner surface of the hook tip ("inner" and "outer" surfaces being referred to herein relative to proximity to the axis of the electrode head) and the confronting surface of the neck portion is slightly greater than or equal to the difference between the radius of the electrode head at a region of full cross-section and the diameter of the fixing hook wire. As previously noted herein, the hook tip may be rounded or pointed, and the point may be disposed at the center of the wire, at the outer surface (FIG. 2), or at the inner surface (FIG. 3). The angle between the fixing hook tip and the beginning of the recess (that is, bounding the opening between the hook tip and the recess surface), relative to the axis of the electrode head and in the direction of rotation for engagement of the hook with cardiac tissue, is less than or equal to 130 degrees in the embodiment of FIGS. 1–3.

Preferably, the electrode head has a stimulation surface 6 adjacent and encompassing the electrode tip, and a further stimulation surface 7 at the surface in the vicinity of the neck region and extending over a large angle $\alpha$ (FIG. 2).

Figure 5:
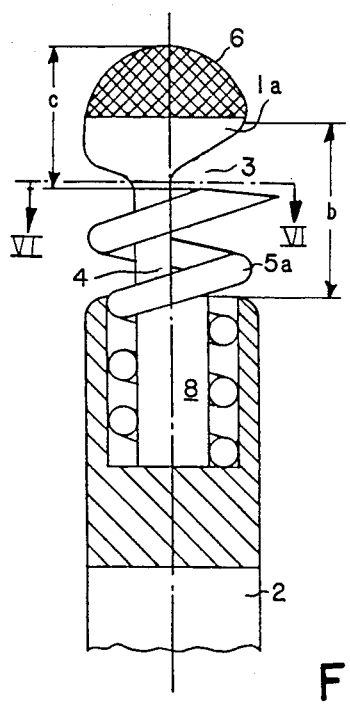
FIG. 5 is a simplified side view of a modified version of the embodiment of FIG. 4 with a partial section through the lead.
Figure 4:
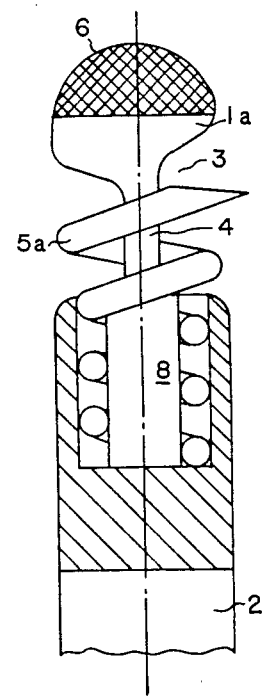
FIG. 4 is a simplified side view of an alternative embodiment of the invention showing the electrode head with a partial section through the lead.
Figure 6:
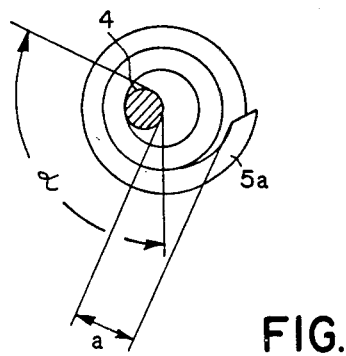
FIG. 6 is a sectional view of the electrode head taken through the plane VI—VI of FIG. 5.

Referring now to FIGS. 4 to 6, in an alternative embodiment of the invention the catheter lead is configured to accommodate the diameter of the spiral shape of a fixing hook 5a, in relatively snug relationship therewith, the spiral being coaxial wit the lead and the head after assembly. A cylindrical portion 8 of an electrode head 1a is configured to be inserted snugly within the spiral of the fixing hook such that the lead, fixing hook and electrode head rotate about the axis of the lead assembly as a single unit. Of course, the electrode head would be electrically coupled within the lead to a coil (not shown) for purposes of cardiac stimulation and/or sensing, and in this respect it will be understood that FIGS. 4 and 5 are simplified views intended only to illustrate the relationship between the fixing hook, the electrode and the lead.

Electrode head 1a is provided with a neck portion 4 which may be concentric with the electrode axis as shown in the embodiment of FIG. 4, or eccentric relative to that axis as shown in the modified version of that embodiment in FIG. 5. The end of the fixing hook 5a of this embodiment lies nearly entirely within the outer contour of the electrode head 1a, protruding only slightly outside that contour at the hook tip as shown most clearly in FIG. 6.

As in the embodiment of FIGS. 1-3, a stimulation surface 6 is provided in this embodiment on the surface of the electrode head 1a adjacent and encompassing the electrode tip, and another or alternative stimulation surface may be provided on the surface of neck portion 4 within the angle α (FIG. 6) substantially opposite the surface of the neck portion confronting the hook tip. In addition, a stimulation surface may be provided by another exposed electrode (not shown) along the circumference of the lead, such as for bipolar stimulation with a cardiac pacemaker.

The measurements and dimensions cited for the earlier-described embodiment are also applicable for the embodiment of FIGS. 4-6, taking into account, however, the concentricity or lesser eccentricity of the neck in these versions of the latter embodiment.

Although certain preferred embodiments of the invention have been described herein, it will be recognized by those skilled in the field to which the invention pertains that variations and other embodiments of the invention may be implemented without departing from the principles of the present invention. Accordingly, it is intended that the invention be limited only to the extent required by the appended claims.

What is claimed is:

1. A catheter lead assembly for intravenous implantation in a selected chamber of the heart of a patient to electrically stimulate the heart from a source of electrical energy, said lead assembly comprising
    an electrode head having a longitudinal axis, a surface portion conducive to electrical stimulation of the heart, and a contour concentric with the axis except along a portion indented toward the axis to form a recess in the head, the head being adapted to be positioned with the said surface portion in electrically stimulating relationship with excitable cardiac tissue after introduction into the selected chamber of the heart,
    a conductive lead including means fastened to the head for electrically connecting the said surface portion to said energy source to deliver electrical energy to said surface portion, the lead having a biocompatible insulating sheath and being adapted to be inserted intravenously into the heart, and
    a rigid hook having a curved portion terminating at one end in means for fastening to the head and at the other end in a tissue-engaging tip, said one end of the hook being secured in fixed relationship to the head, the entire curved portion being configured to lie permanently, without flexing, substantially within the confines of the recess, and the tip being permanently immovable relative to the head and being configured relative to the curved portion of the hook to project slightly from the recess, whereby the lead is adapted to be inserted intravenously for introduction of the head into the selected chamber of the heart without restraint on any portion of the hook beyond said one end being secured to the head, and the tip is adapted, without further deployment, to engage tissue when the head is rotated about the axis by twisting the lead in the direction in which the tip is pointed, for securing the engaged tissue within the recess between the indented portion of the contour and the hook to maintain the said surface portion of the head positioned in stimulating relationship with excitable cardiac tissue in the selected chamber.

2. The lead assembly of claim 1, in which
    said recess is defined by a continuous smooth surface without sharp edges and corners.

3. The lead assembly of claim 2, wherein the tip of the hook is positioned opposite the deepest point of the recess.

4. The lead assembly of claim 3, wherein the distance between the tip of the hook and the deepest point of the recess is equal to or greater than the difference between the radius of the head at the widest portion of the contour and the thickness of the hook.

5. The lead assembly of claim 4, wherein the recess has an axial length equal to or greater than 65% of the diameter of the head at the widest portion of the contour.

6. The lead assembly of claim 5, wherein the axial length of the recess is 80% of the diameter of the head at the said widest portion.

7. The lead assembly of claim 3, wherein the axial distance between the tip of the head and the tip of the hook is greater than or equal to the diameter of the head at the widest portion of the contour.

8. The lead assembly of claim 3, wherein the recess extends through an angle of approximately 270 degrees about the axis of the head.

9. The lead assembly of claim 3, wherein the opening between the tip of the hook and the beginning of the recess in the said direction of rotation is bounded by an angle less than or equal to 130 degrees about the axis of the head.

10. The lead assembly of claim 3, wherein the recess is concentric with the axis of the head.

11. The lead assembly of claim 3, wherein the recess is eccentric with respect to the axis of the head.

12. The lead assembly of claim 3, wherein said one end of the hook is secured to the head at the indented portion of the contour and lies in a plane normal to the axis of the head.

13. The lead assembly of claim 3, wherein said curved portion of the hook has a spiral shape coaxial with the head.

14. The lead assembly of claim 1, wherein at least the tip of the head has the surface conducive to electrical stimulation.

15. The lead assembly of claim 1, wherein at least a part of the head in a circumferential band including the indented portion of the contour has the surface conducive to electrical stimulation.

16. An implantable lead assembly for use in electrical stimulation of the heart, comprising
    an electrode configured for transvenous entry into a selected chamber of the heart and having a conductive surface region adapted to be disposed in electrically stimulating relationship with excitable cardiac tissue in the selected chamber, a transvenous lead fastened to the electrode and including a conductive wire electrically connected to the conductive surface region of the electrode for electrical connection thereof to an electrical stimulus generator, one of the electrode and the lead having a recessed surface adjacent to the electrode tip in proximity to the conductive surface region of the electrode, and a rigid hook including an inflexible curved portion terminating at one end in a tissue-piercing tip, the other end of the hook being secured in fixed relation to the said one of the electrode and the lead having the recessed surface and the hook being otherwise unrestrained for transvenous passage of the lead assembly, the curved portion of the hook being configured relative to the secured end of the hook to lie substantially entirely within the recess with a curvature closely conforming to the contour of the surface immediately adjacent the recessed portion thereof, said hook tip being permanently immovable relative to said electrode and configured relative to said curved portion to protrude slightly from the recess tangentially to said contour for cooperation with the recess to engage cardiac tissue between the hook and the recessed surface when the lead assembly is implanted and twisted about the axis of the lead in the direction in which the hook tip is pointed, whereby to provide fixation of the conductive surface region of the electrode in electrically stimulating relationship with excitable cardiac tissue in the selected chamber of the heart.

17. The lead assembly of claim 16, wherein the conductive surface region is at least at the electrode tip.

* * * * *